(12) United States Patent
Hu et al.

(10) Patent No.: US 9,737,477 B2
(45) Date of Patent: Aug. 22, 2017

(54) ANTI-AGING DIETARY COMPOSITION CONTAINING POLYSACCHARIDES DERIVED FROM GINSENG AND TUBER FLEECEFLOWER ROOT

(71) Applicant: Infinitus (China) Company Ltd., Jiangmen (CN)

(72) Inventors: Minghua Hu, Guangzhou (CN); Ming Liang, Guangzhou (CN); Haifeng Li, Guangzhou (CN); Fangli Ma, Guangdong (CN)

(73) Assignee: Infinitus (China) Company Ltd., Jiangmen, Guangdong (CN)

( * ) Notice: Subject to any disclaimer, the term of this patent is extended or adjusted under 35 U.S.C. 154(b) by 222 days.

(21) Appl. No.: 14/615,441

(22) Filed: Feb. 6, 2015

(65) Prior Publication Data
US 2016/0045428 A1    Feb. 18, 2016

(30) Foreign Application Priority Data

Jul. 28, 2014    (CN) .......................... 2014 1 0361618

(51) Int. Cl.
| | |
|---|---|
| *A01N 65/00* | (2009.01) |
| *A61K 8/97* | (2017.01) |
| *A61Q 19/08* | (2006.01) |
| *A23L 33/105* | (2016.01) |

(52) U.S. Cl.
CPC .............. *A61K 8/97* (2013.01); *A23L 33/105* (2016.08); *A61Q 19/08* (2013.01); *A61K 2800/92* (2013.01)

(58) Field of Classification Search
CPC ...................................................... A61K 36/00
USPC ........................................................ 424/725
See application file for complete search history.

(56) References Cited

FOREIGN PATENT DOCUMENTS

CN        101129748    *    2/2008

* cited by examiner

*Primary Examiner* — Michael Meller
(74) *Attorney, Agent, or Firm* — BEI & OCEAN; George G. Wang

(57) ABSTRACT

The present invention discloses the use of a ginseng and tuber fleeceflower root complex polysaccharide in the preparation of health-care food having anti-aging efficacies, the complex polysaccharide is ginseng and tuber fleeceflower root complex polysaccharide, with ginseng and/or tuber fleeceflower root as raw material, the complex polysaccharide is obtained by water extraction, concentration and alcohol precipitation processes. The complex polysaccharide in the present invention, as proved by *Caenorhabditis elegans* model experiment, is able to prolong the average life span of wild-type, oxidation stress model and protein aggregation toxin model effectively, the effect pathway is closely related to improving anti-oxidation ability in *C. elegans*, inhibiting toxic aggregation protein stress, enhancing the activity of heat-block protein and regulating the crucial node of insulin signalling pathway, which demonstrates that it has good effect of delaying aging and preventing aging-related diseases.

1 Claim, 10 Drawing Sheets

ANTI-AGING DIETARY COMPOSITION CONTAINING POLYSACCHARIDES DERIVED FROM GINSENG AND TUBER FLEECEFLOWER ROOT

FIELD OF THE INVENTION

The present invention relates to the technical field of health-care food, and specifically relates to the use of a ginseng and tuber fleeceflower root complex polysaccharide in the preparation of health-care dietary supplements having anti-aging effects.

BACKGROUND OF THE INVENTION

Recent researches show that aging results from interaction of various stress factors in vivo and in vitro, in the mean time these stress conditions and aging itself are also the important influencing factors during the pathological processes of various diseases. For example, oxidation stress, and toxic aggregation protein are closely related to aging of organism and various diseases such as neurodegenerative disease and tumors. Although aging is naturally inevitable, it is possible to delay aging. As the global population aging is becoming increasingly severe, the incidences of aging-related diseases are increasing every year. In addition to treating existing diseases and disorders by means of medicine, the necessity and demand for preventive measures for staying healthy and delaying aging is increasing. Therefore, strengthening the strategic study of delaying aging and prevention of aging-related diseases has great significance to maintain quality of life, and has become the current R&D focus and hotspot of the health-care industry.

*Caenorhabditis elegans* (*C. elegans*) is a model animal commonly used for studying aging and related diseases, which has prominent advantages such as, short life cycle, simple experimental manipulation, and rich genetic resources. In addition, it is the first multicellular organism whose full genome sequencing has been completed, whose genome comprises ⅔ of human disease-related genes, and transgenic disease models can be easily obstructed, by means of GFP labelling and whole-genome RNAi technology, it is possible to conduct a systematic and complete life-long follow-up research on degenerative pathology and potential medicament at the individual level, which is especially important to the study of aging and relative diseases. Therefore, the use of *C. elegans* greatly promotes the explanation of aging-related pathological mechanisms and the development of active compound.

China's abundant herbal species provides a broad resource library for measures of delaying aging and preventing relative neurodegenerative disease, wherein the medicine edible species undoubtedly have huge medical medicinal and nutrition health care values. For example, ginseng is a Chinese traditional Qi supplementing-type Traditional Chinese Medicine, having the efficacies such as supplementing Spleen and Lung tonifying, quieting the spirit and boosting the mind, supplementing Yuan for relieving desertion, engendering Liquid and allaying thirst; tuber fleeceflower root being a famous Blood supplementing-type Traditional Chinese Medicine, has the anti-aging effects e.g., supplementing Liver and Kidney, boosting Essence and Blood, blackening the beard and hair, and strengthening sinew and bones. Recent researches show that the polysaccharides originated from these anti-aging Chinese herbal medicines also have potential biological activities for delaying aging and preventing relative diseases. However, since the occurrence and development of aging and relative diseases thereof are multiple-factor triggered, complex and latent, a single polysaccharide might has the defects e.g., limited effect target and inadequate active function, thus enlarging and enhancing the activity of polysaccharide is indispensable for further development and improvement of polysaccharide-type product. The recent researches show that, the combined administration of Radix Astragali polysaccharide and sulfated epimedium polysaccharide can improve the function of chicken immune system, therefore relieving the immunosuppression caused by cyclophosphamide; Manyprickle Acathopanax Root polysaccharide may synergically enhance the therapeutic effect of metformin to diabetic mice. These researches show that the combined administration of the polysaccharides of Traditional Chinese Medicine with other compounds or the complex polysaccharide has the effects of enhancing therapeutic effects. Therefore, strengthening the research of complex polysaccharide with respect to anti-aging efficacies not only benefits for promoting its in-depth application in the medicinal health care field, expanding the application extent of polysaccharide product, but also provides novel active substance for preventing aging and relative diseases thereof.

SUMMARY OF THE INVENTION

The purpose of present invention is to provide the use of a ginseng and tuber fleeceflower root complex polysaccharide in the preparation of health-care dietary supplement (also known as health food or functional food) having anti-aging efficacies.

The aforesaid purpose of the present invention is achieved by the following technical solution: the use of aforesaid ginseng and tuber fleeceflower root complex polysaccharide in the preparation of health-care food (health food or functional food) having anti-aging efficacies.

The mass ratio of ginseng polysaccharide and tuber fleeceflower root polysaccharide in the ginseng and tuber fleeceflower root complex polysaccharide according to the present invention is preferably 1:4-9:1, and further preferably 2:3-2:1.

Preferable preparation method: with ginseng and tuber fleeceflower root as raw material, complex polysaccharide is prepared by processes including water extraction, concentration and alcohol precipitation. The resulting complex polysaccharide has an anti-aging effect, and can be used for preparing the health-care food.

In the preparation of the ginseng and tuber fleeceflower root complex polysaccharide according to the present invention:

The mass ratio of ginseng and tuber fleeceflower root according to the present invention is preferably 1:4-9:1.

The mass ratio of ginseng and tuber fleeceflower root according to the present invention is more preferably 2:3-2:1.

For water extraction, the mass volume ratio of ginseng and tuber fleeceflower root medicinal material with water is 1:2-1:20, the extraction temperature is 50-100° C., the extraction duration is 1-10 h. For concentration, the temperature is 40-100° C. For alcohol precipitation, the volume ratio of the ethanol to the concentrated liquid is 2:1-9:1.

Ginseng refers to the root part of ginseng, tuber fleeceflower root refers to its tuber root part.

Another preferable preparation method: with ginseng or tuber fleeceflower root as raw material, ginseng polysaccharide or tuber fleeceflower root polysaccharide is prepared separately by processes including water extraction, concentration and alcohol precipitation. Then, these two polysaccharides are mixed in a stoichiometric ratio, to prepare the ginseng and tuber fleeceflower root complex polysaccharide, the complex polysaccharide has an anti-aging effect, can be used for preparing the health-care food having anti-aging efficacies.

In the preparation method of the ginseng and tuber fleeceflower root complex polysaccharide:

For water extraction, the mass volume ratio of ginseng/tuber fleeceflower root medicinal material to water is 1:2-1:20, the extraction temperature is 50-100° C., the extraction duration is 1-10 h. For concentration, the temperature is 40-100° C. For alcohol precipitation, the volume ratio of ethanol to the concentrated liquid is 2:1-9:1.

The mass ratio of ginseng polysaccharide and tuber fleeceflower root polysaccharide in the ginseng and tuber fleeceflower root complex polysaccharide is preferably 1:4-9:1.

The mass ratio of ginseng polysaccharide and tuber fleeceflower root polysaccharide in the ginseng and tuber fleeceflower root complex polysaccharide is further preferably 2:3-2:1.

Ginseng refers to the medicinal root part of ginseng, tuber fleeceflower root refers to the medicinal tuber root part of tuber fleeceflower root.

The anti-aging efficacies according to the present invention refers to the prolongation of life span of organisms under stress factors in vivo and in vitro and the relief of symptoms induced by these stress factors.

The ginseng and tuber fleeceflower root complex polysaccharide provided by the present invention has anti-aging efficacies, specifically represented by capable of prolonging the life span of C. elegans model under the conditions of normal aging, oxidation stress, and toxic protein stress on the level of entire animal, the effecting manner is closely related to reducing the reactive oxygen species level and lipid peroxide content, improving the activity of antioxidant enzyme, inhibiting polyglutamine and β-amyloid aggregation and toxicity hereof, enhancing the activity of heat-block protein and regulating the crucial node of insulin signalling pathway in C. elegans, thus can be used for delaying aging and preventing the aging-related diseases whose major pathological mechanism is oxidation stress and abnormal protein aggregation.

The dosage form of the health-care food according to the present invention can be capsule, powder, granule, tablet or oral liquid etc. For example, to the aforesaid complex polysaccharide, other raw materials such as lactalbumin, supplement such as maltodextrin can be added, to prepare the health food or health-care food having anti-aging efficacies.

The present invention has the following advantages:

(1) The ginseng and tuber fleeceflower root complex polysaccharide in the present invention, the preparation process thereof is concise and complete, stable and efficient, suitable for mass production;

(2) The ginseng and tuber fleeceflower root complex polysaccharide prepared by the present invention is proved to be able to delay aging on the level of entire animal of C. elegans, has an inhibitory effect upon each of aging-related oxidation stress, abnormal aggregation of protein and toxicity thereof, is demonstrated that it can be used in the solid or liquid preparation of health food or health-care food having anti-aging efficacies, provides a novel solution for preventing aging-related diseases and healthy aging, and promotes the in-depth application of polysaccharide product and modernized development of Traditional Chinese Medicine.

BRIEF DESCRIPTION OF THE DRAWINGS

Hereinbelow the present invention will be further demonstrated by embodiments and pharmacodynamic research results.

Detailed description of particular embodiments of the invention Hereinafter part of specific examples are listed to describe the present invention, it is necessary to point out here that the following examples are only for further explaining the present invention, are not deemed as limitation to the protection scope of the present invention. Some non-substantial change and modification made by others according to the present invention still belong to the protection scope of the present invention.

EXAMPLE 1

The ginseng and tuber fleeceflower root complex polysaccharide provided by this example, is prepared by the following method: ginseng and tuber fleeceflower root medicinal materials are mixed in a mass ratio of 1:1, wherein ginseng refers to the medicinal root part of ginseng, tuber fleeceflower root refers to the medicinal tuber root part of tuber fleeceflower root, sic passim, after pulverization, water is added in a material liquid ratio of 1:10 (g/mL), stirred and heated under 90° C. for extracting for 4 h. To the medicine dregs obtained upon filtration, water is added in a material liquid ratio of 1:5 (g/mL), the extraction continues for 4 h under 90° C. Two extract liquid are combined, upon decompression concentration and centrifugation, clear concentrate liquid is obtained, to the concentrate liquid, 95% (volume percentage, sic passim) ethanol in a 4-fold volume is added in a volume ratio of 1:4, after mixed homogeneously, stood overnight at 4° C. for precipitation, the precipitate is collected by centrifugation, then the complex polysaccharide is obtained through vacuum freeze-drying.

Alternatively, to the ginseng after pulverization, water is added in a material liquid ratio of 1:10 (g/mL), stirred and heated under 90° C. for extracting for 4 h. To the medicine dregs obtained upon filtration, water is added in a material liquid ratio of 1:5 (g/mL), the extraction continues for 4 h under 90° C. Two extract liquid are combined, upon decompression concentration and centrifugation, clear concentrate liquid is obtained, to the concentrate liquid, 95% ethanol in a 4-fold volume is added in a volume ratio of 1:4, after mixed homogeneously, stood overnight at 4° C. for precipitation, the precipitate is collected by centrifugation, then ginseng polysaccharide is obtained through vacuum freeze-drying, the preparation method of tuber fleeceflower root polysaccharide is the same as that of ginseng polysaccharide, tuber fleeceflower root polysaccharide and ginseng polysaccharide are mixed homogenously in a mass ratio of 1:1, to prepare the ginseng and tuber fleeceflower root complex polysaccharide.

The ginseng and tuber fleeceflower root complex polysaccharide prepared by the first method and the second method, are substantially the same in features, the ginseng and tuber fleeceflower root complex polysaccharide prepared by either method can be used.

EXAMPLE 2

The ginseng and tuber fleeceflower root complex polysaccharide provided by this example, is prepared by the following method: ginseng and tuber fleeceflower root medicinal material are mixed in a mass ratio of 2:3, after pulverization, water is added in a material liquid ratio of 1:15 (g/mL), stirred and heated under 90° C. for extracting for 6 h. Clear concentrate liquid is obtained by centrifugation after decompression concentration, to the concentrate liquid, 95% ethanol in a 3-fold volume is added in a volume ratio of 1:3, after mixed homogeneously, stood overnight at 4° C. for precipitation, the precipitate is collected by centrifugation, then the complex polysaccharide is obtained through vacuum freeze-drying.

This Example also can utilize ginseng or tuber fleeceflower root as respective raw material the same as in Example 1, to prepare ginseng and tuber fleeceflower root complex polysaccharide.

EXAMPLE 3

The ginseng and tuber fleeceflower root complex polysaccharide provided by this example, is prepared by the following method: ginseng and tuber fleeceflower root medicinal material are mixed in a mass ratio of 3:2, after pulverization, water is added in a material liquid ratio of 1:10 (g/mL), stirred and heated under 95° C. for extracting for 3 h. The medicine dregs obtained upon filtration is extracted once again in the aforesaid material liquid ratio, temperature and duration. Two extract liquids are combined, upon decompression concentration and centrifugation, clear concentrate liquid is obtained, to the concentrate liquid, 95% ethanol in a 2-fold volume is added in a volume ratio of 1:2, after mixed homogeneously, stood overnight at 4° C. for precipitation, the precipitate is collected by centrifugation, then the complex polysaccharide is obtained through vacuum freeze-drying.

This Example also can utilize ginseng or tuber fleeceflower root as respective raw material the same as in Example 1, to prepare ginseng and tuber fleeceflower root complex polysaccharide.

EXAMPLE 4

The ginseng and tuber fleeceflower root complex polysaccharide provided by this example, is prepared by the following method: ginseng and tuber fleeceflower root medicinal material are mixed in a mass ratio of 2:1, after pulverization, water is added in a material liquid ratio of 1:5 (g/mL), stirred and heated under 75° C. for extracting for 3 h The medicine dregs obtained upon filtration is extracted twice again in the aforesaid material liquid ratio, temperature and duration. Three extract liquids are combined, upon decompression concentration and centrifugation, clear concentrate liquid is obtained, to the concentrate liquid, 95% ethanol in a 9-fold volume is added in a volume ratio of 1:9, after mixed homogeneously, stood overnight at 4° C. for precipitation, the precipitate is collected by centrifugation, then the complex polysaccharide is obtained through vacuum freeze-drying.

This Example also can utilize ginseng or tuber fleeceflower root as respective raw material the same as in Example 1, to prepare ginseng and tuber fleeceflower root complex polysaccharide.

EXAMPLE 5

The ginseng and tuber fleeceflower root complex polysaccharide provided by this example, is prepared by the following method: ginseng and tuber fleeceflower root medicinal material are mixed in a mass ratio of 4:1, after pulverization, water is added in a material liquid ratio of 1:20 (g/mL), stirred and heated under 80° C. for extracting for 10 h. Clear concentrate liquid is obtained by centrifugation after decompression concentration, to the concentrate liquid, 95% ethanol in a 4-fold volume is added in a volume ratio of 1:4, after mixed homogeneously, stood overnight at 4° C. for precipitation, the precipitate is collected by centrifugation, then the complex polysaccharide is obtained through vacuum freeze-drying.

This Example also can utilize ginseng or tuber fleeceflower root as respective raw material the same as in Example 1, to prepare ginseng and tuber fleeceflower root complex polysaccharide.

EXAMPLE 6

The ginseng and tuber fleeceflower root complex polysaccharide provided by this example, is prepared by the following method: ginseng and tuber fleeceflower root medicinal material are mixed in a mass ratio of 9:1, after pulverization, water is added in a material liquid ratio of 1:15 (g/mL), stirred and heated under 50° C. for extracting for 1 h, extracted for 3 times, the filtrates are combined, clear concentrate liquid is obtained by centrifugation after decompression concentration, to the concentrate liquid, 95% ethanol in a 0.5-fold volume is added in a volume ratio of 2:1, after mixed homogeneously, stood overnight at 4° C. for precipitation, the precipitate is collected by centrifugation, then the complex polysaccharide is obtained through vacuum freeze-drying.

This Example also can utilize ginseng or tuber fleeceflower root as respective raw material the same as in Example 1, to prepare ginseng and tuber fleeceflower root complex polysaccharide.

EXAMPLE 7

The length of life span is one of the most direct and important indicators for measuring organism aging. Thus, by studying the regulation effect of complex polysaccharide under normal and stress conditions on the life span of *C. elegans*, it is possible to determine directly whether the polysaccharide has a potential activity for delaying aging and alleviating aging-related disorders. Firstly, abundant wild-type *C. elegans* N2 in L1 Phase are made available by synchronized manipulation, then S Medium is added to adjust the *C. elegans* density to 10-20/10 μL, then *E. coli* OP50 is added to make OD570≈0.4, after cultivated under 20° C. for 42-45 h, *C. elegans* enters into L4 Phase. To appropriate amount of *C. elegans* solution, S Medium is added to dilute the *C. elegans* density to 10-20/100 μL, meanwhile OP50 is supplemented to make OD570≈0.6, then 100 μg/mL of 5-FUDR solution, 50 μg/mL of carbenicillin solution and 0.1 μg/mL of Amphotericin solution are added by turn, the cultivation of adjusted *C. elegans* solution continues under 20° C. for 2 d till imaginal initial phase. The *C. elegans* solution is added in 90 μL/well into a 96-well plate, 10 μL of the complex polysaccharide prepared by Example 1 is added to complex polysaccharide group, 10 μL of ginseng polysaccharide and tuber fleeceflower root polysaccharide prepared by Example 1 is respectively added to the single polysaccharide group, the final concentration of each of complex polysaccharide and single polysaccharide is 2 mg/mL. 10 μL of S Medium is added to control group. 10 parallel wells are set for each of polysaccharide group and control group, then sealed with parafilm, shook on microplate reader for 30 sec to make polysaccharide and *C. elegans* solution mix homogenously. The available 96-well plate is cultivated under 20° C., the start-up day of administration is regarded as Day 0, the survival status of *C. elegans* in each well is statistically counted every 2 d, until all of them die. The *C. elegans*, whose body is stiff, still and no response to slight shake, is determined as in a death status during statistically counting process. The survival rate of *C. elegans* is analyzed by Kaplan-Meier method, and the difference between polysaccharide group and control group is compared by log-rank test.

Figure 1:
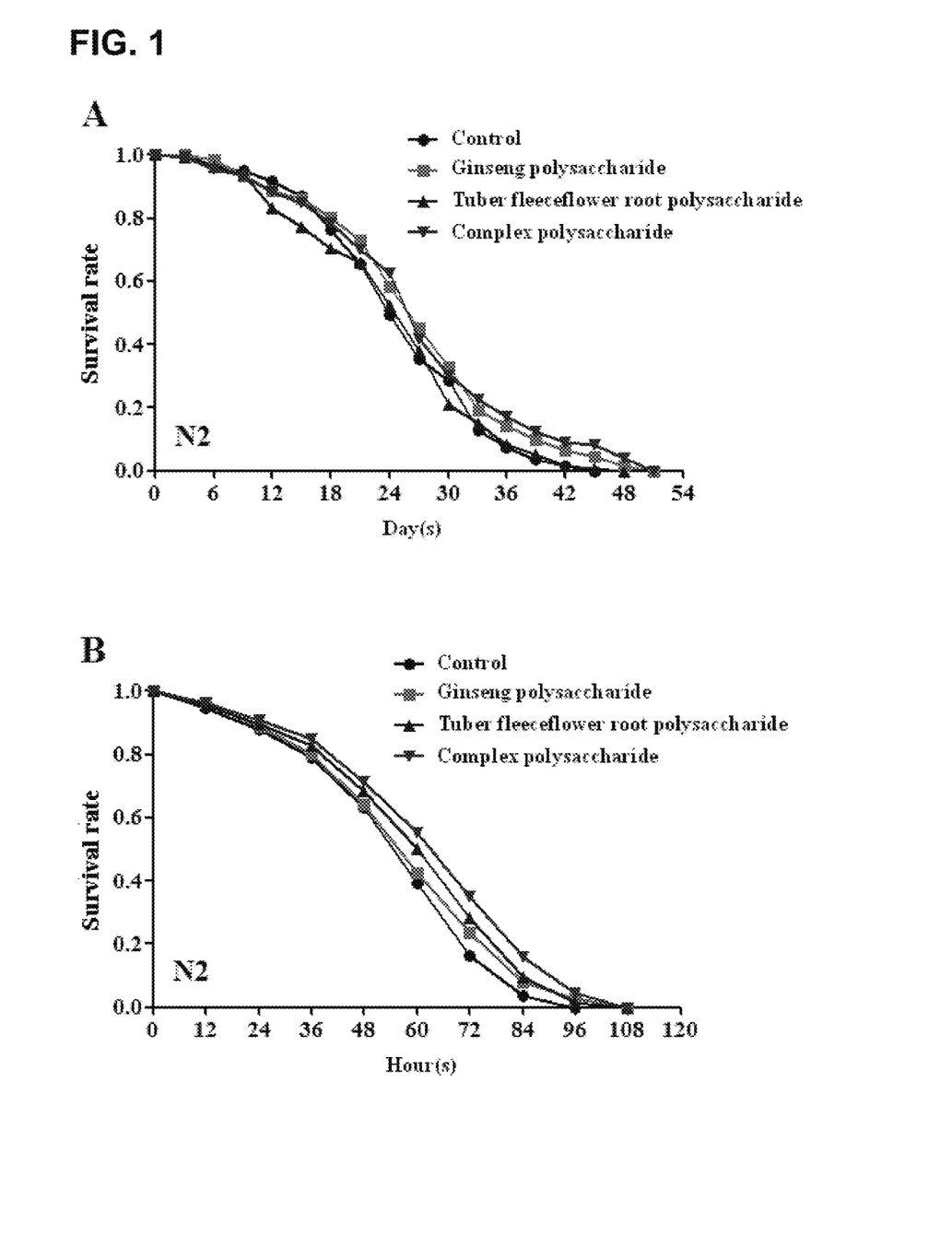
FIG. 1 is a characterization figure of the data of the effects of utilizing the ginseng and tuber fleeceflower root complex polysaccharide and a single polysaccharide in Example 1, under normal, oxidation stress and toxic protein stress conditions, on the life span of C. elegans in Example 7, wherein FIG. 1A characterizes the prolongation effect of 2 mg/mL of complex polysaccharide, ginseng polysaccharide and tuber fleeceflower root polysaccharide on the life span of C. elegans N2, FIG. 1B characterizes the prolongation effect of 2 mg/mL of complex polysaccharide, ginseng polysaccharide and tuber fleeceflower root polysaccharide under paraquat oxidation stress on the life span of C. elegans N2, FIG. 1C characterizes the prolongation effect of 2 mg/mL of complex polysaccharide, ginseng polysaccharide and tuber fleeceflower root polysaccharide on the life span of C. elegans CL2355, FIG. 1D characterizes the prolongation effect of 2 mg/mL of complex polysaccharide, ginseng polysaccharide and tuber fleeceflower root polysaccharide on the life span of C. elegans HA759.

The results are as shown in FIG. 1A, under normal condition, the average life span of wild-type *C. elegans* N2 is 23.6 d. Upon administration of 2 mg/mL polysaccharide, each of complex polysaccharide (26.9 d) and ginseng polysaccharide (26.3 d) shows prolongation effect on the life span, while tuber fleeceflower root polysaccharide (23.2 d) has little effect on the life span of *C. elegans*.

Free radical theory is one of the most authorized theories having been broadly studied and proved with respect to aging mechanism. The theory believes that, the oxidation stress induced by abundant free radicals breaks down the structure and function of macromolecules such as intracellular nucleic acid, protein and lipids, is capable of causing cellular dysfunction even decaying death. Although oxidation stress is not the only factor resulting in aging, it plays a crucial role during the occurrence and development process of aging and various relative diseases. Thus, reducing oxidation stress is undoubtedly benefit for delaying aging and the relief of aging-related disorders. The complex polysaccharide prepared by Example 1, in a concentration of 2 mg/mL, is added to the 5-FUDR treated L4-Phase N2 lavae, meanwhile an oxidation stress model is established with 100 mM of paraquat. To the single polysaccharide group, the ginseng polysaccharide and tuber fleeceflower root polysaccharide prepared in Example 1 is added respectively, in a respective polysaccharide concentration of 2 mg/mL. To the control group, equal volume of polysaccharide solution is substituted by S Medium. After administration, cultivated at 20° C., the time point adding polysaccharide and paraquat is counted as 0 h, the survival status of *C. elegans* is statistically counted every 12 h, until all of them die. The determination of the death status and the statistical method of the survival rate of *C. elegans* are as hereinbefore.

The results are as shown in FIG. 1B, the acute oxidation stress caused by paraquat will result in quick death of *C. elegans*, the average survival duration of control group is 55.2 h, and after the respective treatment utilizing 2 mg/mL of complex polysaccharide, ginseng polysaccharide and tuber fleeceflower root polysaccharide, the average survival duration of *C. elegans* is prolonged to 64.1 h. 59.7 h and 62.8 h. In comparison with a single polysaccharide treatment, the prolongation effect of complex polysaccharide under oxidation stress on life span is more significant.

Dynamic balance of protein is an important condition for maintaining cellular physiological function. Research show that, affected by the stress caused by the change in the outer surrounding and in vivo physiological condition, the biochemical processes such as synthesis, modification, folding and degradation of cellular protein is often affected, thus the dynamic balance of protein is broken, influencing the performance of normal physiological function and inducing cellular senescent and pathology. With the crucial pathological protein Aβ42 (β-amyloid 42 fragment, β-amyloid peptide 42, Aβ42) and polyQ (polyglutamine, polyQ) in the common senile diseases such as Alzheimer's Disease and Huntington's Disease as toxic inducers, by expressing these toxic aggregation-feasible proteins in C. elegans to induce aging-related disorders, for example, life span shortening and behavior abnormality etc., so that the alleviation effect of complex polysaccharide on the symptoms of aging-related diseases is studied. The complex polysaccharide prepared by Example 1, in a concentration of 2 mg/mL, is added to 5-FUDR treated L4 Phase CL2355 (pan-neuron expresses Aβ42) and HA759 (ASH neuron expresses polyQ40) larvae, respectively. The ginseng polysaccharide and tuber fleeceflower root polysaccharide prepared by Example 1 is added to the single polysaccharide group, respectively, each in a polysaccharide concentration of 2 mg/mL. In control group, an equal volume of S Medium is used to substitute polysaccharide solution. The available 96-well plate is cultivated under 20° C., the start-up day of administration is regarded as Day 0, the survival status of C. elegans in each well is statistically counted every 2 d, until all of them die. The determination of the death status and the statistical method of the survival rate of C. elegans are as hereinbefore.

The results are as shown in FIGS. 1C and 1D, under toxic aggregation protein stress condition, the average life span of CL2355 C. elegans is 21.4 d. upon respective treatment of 2 mg/mL of complex polysaccharide and ginseng polysaccharide, the average life span of C. elegans is prolonged to 23.8 d and 22.5 d, while 2 mg/mL of tuber fleeceflower root polysaccharide (21.7 d) cannot prolong the average life span of CL2355 C. elegans; with respect to HA759 C. elegans, complex polysaccharide, ginseng polysaccharide and tuber fleeceflower root polysaccharide is able to prolong its average life span from 22.9 d to 25.5 d, 24.6 d and 24.3 d, respectively. In comparison with a single polysaccharide treatment, the prolongation effect of complex polysaccharide on the life span under toxic protein stress is more significant.

The aforesaid results show that, complex polysaccharide is capable of prolonging the life span of C. elegans significantly under normal condition, oxidation stress condition, and toxic protein stress condition on the level of entire animal, which demonstrates that it has good anti-aging effect.

EXAMPLE 8

According to the viewpoint of free radical theory, reducing reactive oxygen species (ROS) level will be of help for reducing oxidation stress injury, and maybe of help to the delaying of aging. The complex polysaccharide prepared by Example 2, is added in a concentration of 1 mg/mL, 2 mg/mL and 4 mg/mL to L1 Phase N2, CL2355 and HA759 larvae, respectively. To control group, an equal volume of S Medium is added. C. elegans is collected after cultivation under 15° C. for 3 d, then 1% Tween 20-comprising PBS is added, after homogenized on ice, DCFH-DA probe solution (ROS level indicator) is added, incubated under 37° C. in dark, then the fluorescent value is detected by fluorescent microplate reader, with excitation wavelength being 485 nm, emission wavelength being 530 nm. Relative fluorescent density is represented by mean±SEM, T test is used to compare the difference between complex polysaccharide group and control group.

Figure 2:
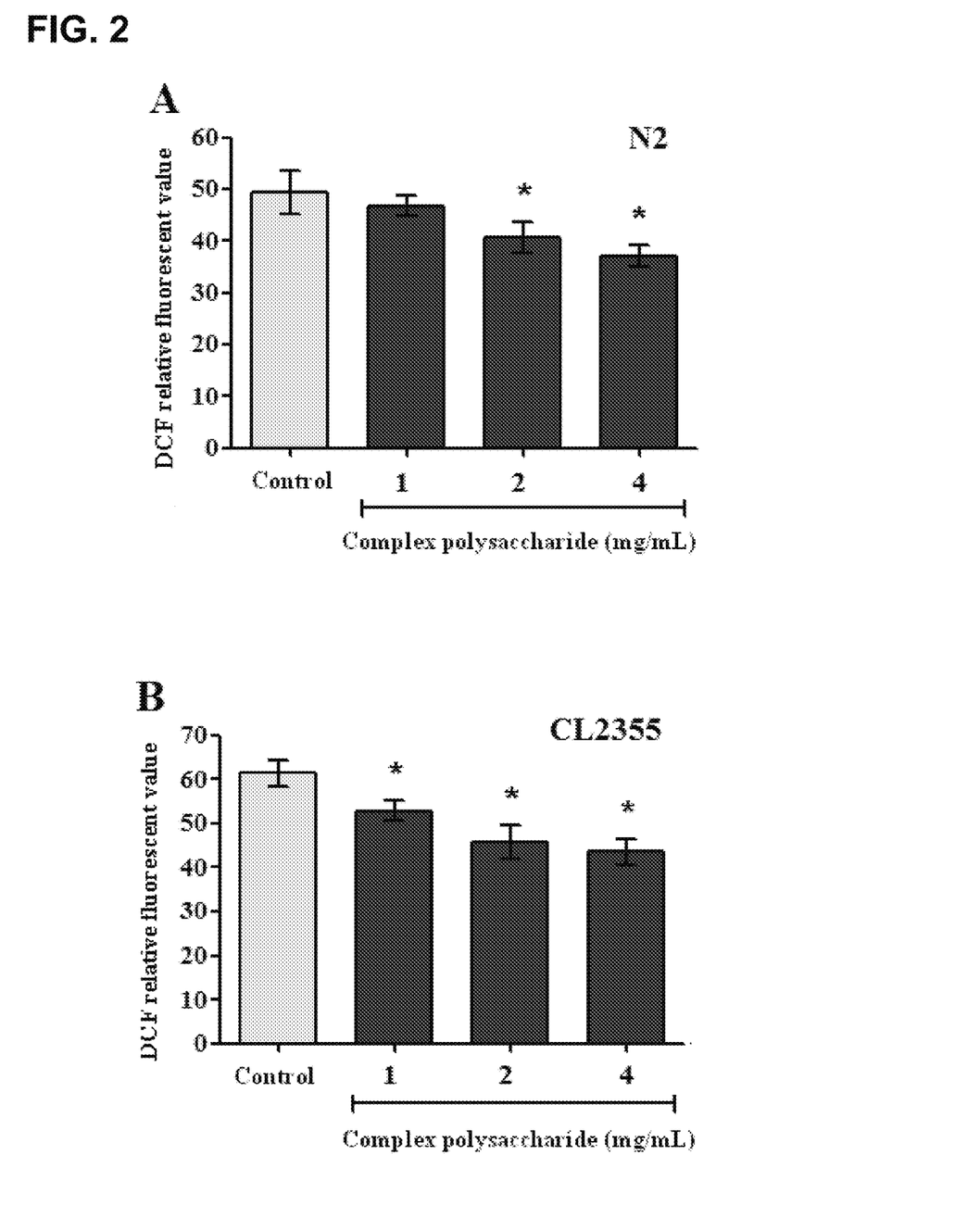
FIG. 2 is a characterization figure of the data of utilizing the ginseng and tuber fleeceflower root complex polysaccharide of Example 2 for reducing the reactive oxygen species level in the C. elegans in Example 8, wherein FIG. 2A characterizes 1 mg/mL, 2 mg/mL and 4 mg/mL of complex polysaccharide for reducing the reactive oxygen species level in the C. elegans N2, FIG. 2B characterizes 1 mg/mL, 2 mg/mL and 4 mg/mL of complex polysaccharide for reducing the reactive oxygen species level in the C. elegans CL2355, FIG. 2C characterizes 1 mg/mL, 2 mg/mL and 4 mg/mL of complex polysaccharide for reducing the reactive oxygen species level in the C. elegans HA759, wherein * represents $p<0.05$.

The results are as shown in FIG. 2, the DCF relative fluorescent value of N2 C. elegans is 49.3, the treatment of 2 mg/mL and 4 mg/mL of complex polysaccharide is able to reduce DCF relative fluorescent value to 40.7 and 36.9, respectively; the DCF relative fluorescent value of CL2355 C. elegans is 61.3, after the treatment of 1 mg/mL, 2 mg/mL and 4 mg/mL of complex polysaccharide, DCF relative fluorescent value is reduced to 52.8, 45.7 and 43.5, respectively; the DCF relative fluorescent value of HA759 C. elegans is 53.9, the treatment of 2 mg/mL and 4 mg/mL of complex polysaccharide is able to reduce DCF relative fluorescent value to 44.2 and 42.5, respectively. These results show that complex polysaccharide is able to reduce the ROS level of C. elegans in vivo significantly, and has a good anti-oxidation activity in vivo.

EXAMPLE 9

Since oxidation injury is related to ROS level and oxidation product, by improving ROS clearance ability (e.g., antioxidant enzyme) and reducing peroxide product (e.g., malondialdehyde), it is able to achieve the purpose of reducing oxidation injury. Firstly, the N2, CL2355 and HA759 C. elegans in imaginal initial phase are prepared, the C. elegans density is adjusted to 40-50/100 μL, then the C. elegans solution is added into a 24-well plate in 0.9 mL/well, the cultivation under 25° C. continues for 18 d. The complex polysaccharide prepared by Example 2, is added to C. elegans in a concentration of 2 mg/mL, 0.1 mL of S Medium is added to control group. After the cultivation under 25° C. continues for 2 d, C. elegans solution is collected and centrifuged to obtain C. elegans, then 1 mL of pre-cooled S Medium is added to resuspend C. elegans, then 1 mL of pre-cooled 60% sucrose solution is added, after mixed homogenously, centrifuged within 5 min, the liquid with C. elegans floated on the top layer is absorbed, then washed with 1 mL of S Medium for 3 times to remove sucrose. 1 mL of PBS is used to resuspend C. elegans, then ultrasonically homogenized in an ice water bath for 10 min. The supernatant, i.e., enzyme solution is collected by centrifugation, BCA protein quantification assay is used to detect the concentration of protein, and Beyotime assay kit is used to detect the activities of superoxide dismutase (SOD), catalase (CAT), glutathione peroxidase (GPX) and malondialdehyde (MDA) content, respectively.

The results are as shown in the following Table 1, compared with untreated C. elegans N2, complex polysaccharide is able to improve the activities of SOD and GPX and reduce MDA content significantly; with respect to CL2355 and HA759 C. elegans, complex polysaccharide is able to improve the activities of SOD, CAT and GPX and reduce MDA content significantly. These results show that complex polysaccharide is able to clear ROS and reduce oxidation injury by improving the anti-oxidation ability and reducing peroxide product of C. elegans, has a good anti-oxidation activity in vivo.

| C. elegans strain | treatment | antioxidant enzyme activities | | | MDA content (nM/mg protein) |
|---|---|---|---|---|---|
| | | SOD (U/mg protein) | CAT (k/mg protein) | GPX (U/mg protein) | |
| N2 | control | 26.2 ± 1.03 | 34.8 ± 1.27 | 13.5 ± 1.19 | 2.53 ± 0.17 |
| | complex polysaccharide | 30.2 ± 0.86* | 35.4 ± 0.96 | 16.9 ± 0.32* | 2.05 ± 0.08* |
| CL2355 | control | 30.6 ± 1.68 | 36.1 ± 1.63 | 16.2 ± 0.89 | 2.86 ± 0.23 |
| | complex polysaccharide | 35.4 ± 1.02* | 40.8 ± 0.79* | 19.4 ± 0.64* | 1.95 ± 0.12* |
| HA759 | control | 23.8 ± 0.61 | 32.7 ± 0.58 | 17.3 ± 0.49 | 2.09 ± 0.16 |
| | complex polysaccharide | 27.9 ± 0.53* | 37.4 ± 1.07* | 21.7 ± 1.21* | 1.73 ± 0.07* | wherein * represents $p < 0.05$.

EXAMPLE 10

Transgenic *C. elegans* CL2355 expresses A1342 protein in the neuron in vivo, its aggregation is able to produce significant neuronal toxicity, thus results in the reduction of the chemotactic behavior ability of *C. elegans*, thus this model may be used to study the alleviation effect of complex polysaccharide on toxic protein stress. The complex polysaccharide prepared by Example 3, in a concentration of 1 mg/mL, 2 mg/mL and 4 mg/mL, is added to L1 phase CL2355 larvae, respectively, an equal volume of S Medium is added to control group. After cultivation under 16° C. for 36 h, transferred to 23° C. for further cultivation for 36 h. A 9 cm culture dish is taken, with a straight line drawn with 1 mol/L glycerol within for division, in the left half round region, 1.5 μL of 0.5% benzaldehyde in ethanol solution and 1.5 μL of 1 mol/L solution of sodium azide are added, and labeled as A zone. In the same position of the right half round region, 1.5 μL of ethanol and 1.5 μL of 1 mol/L solution of sodium azide are added, and labeled as B zone. After CL2355 *C. elegans* is transferred to the center of culture dish, incubated under 23° C. for 1 h, then the *C. elegans* numbers in A zone and B zone are statistically analyzed respectively, chemotactic rate=(A zone number−B zone number)/total number of *C. elegans*. Data is represented by mean±SD, T test is used to compare the difference between polysaccharide group and control group.

Figure 3:
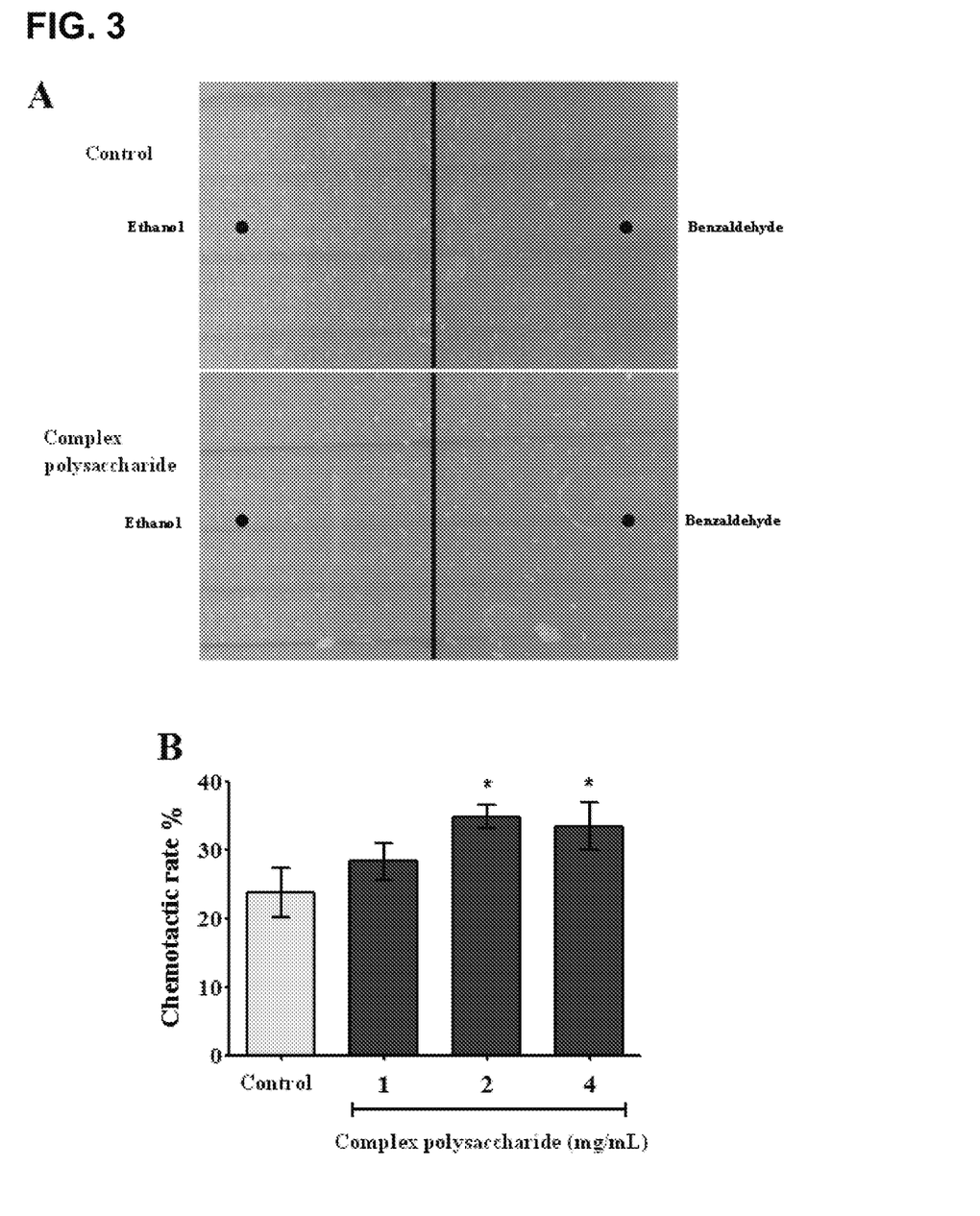
FIG. 3 is a characterization figure of the data of utilizing the ginseng and tuber fleeceflower root complex polysaccharide in Example 3 for inhibiting the toxicity of β-amyloid in C. elegans CL2355 in vivo in Example 10, wherein FIG. 3A characterizes the representative figure of the effect of 2 mg/mL of complex polysaccharide on the chemotactic behavior of C. elegans CL2355, FIG. 3B characterizes 1 mg/mL, 2 mg/mL and 4 mg/mL of complex polysaccharide for alleviating the chemotactic ability of C. elegans CL2355, wherein * represents $p<0.05$.

The results are as shown in FIG. 3A, in comparison with control, the number of complex polysaccharide treated CL2355 *C. elegans* in the benzaldehyde region is more. The statistical results of FIG. 3B show that, the chemotactic rate of untreated CL2355 *C. elegans* is merely 23.8%, while the chemotactic rate of complex polysaccharide in a concentration of 2 mg/mL and 4 mg/mL can be improved to 34.9% and 33.5%, respectively, which demonstrate s that complex polysaccharide is able to improve behavior defect induced by toxic protein Aβ stress, and has an effect of alleviating aging-related disorders.

EXAMPLE 11

*C. elegans* transgenic model HA759 promotes polyQ40 fragment to be expressed in its head portion ASH neuron by utilizing osmosis-related gene osm-10, since the aggregation of polyQ40 is able to cause significant toxicity, progressive apoptosis takes place in ASH neuron (shown as fluorescent disappearance). Thus, it is possible to study the alleviation effect of complex polysaccharide on toxic aggregation protein stress by observing the survival rate of ASH neuron. The complex polysaccharide prepared by Example 3, in a concentration of 1 mg/mL, 2 mg/mL and 4 mg/mL, is added to L1 Phase HA759 larvae, respectively, an equal volume of S Medium is added to control group. After cultivation under 15° C. for 3 d, *C. elegans* is collected, solution of sodium azide is added to make *C. elegans* paralyzed, after mixed homogenously, added in droplet on the agarose pad, the GFP fluorescent point in each *C. elegans* ASH neuron is observed under a fluorescent microscope. About 50 *C. elegans* are statistically analyzed in each treatment group, survival percentage of ASH neuron=*C. elegans* number with survived ASH neuron/(*C. elegans* number with survived ASH neuron+*C. elegans* number with ASH neuron dead)×100%. Survival rate is represented by mean±SEM, one-way ANOVA analysis and Tukey post-hoc test are used to compare the difference between polysaccharide group and control group.

Figure 4:
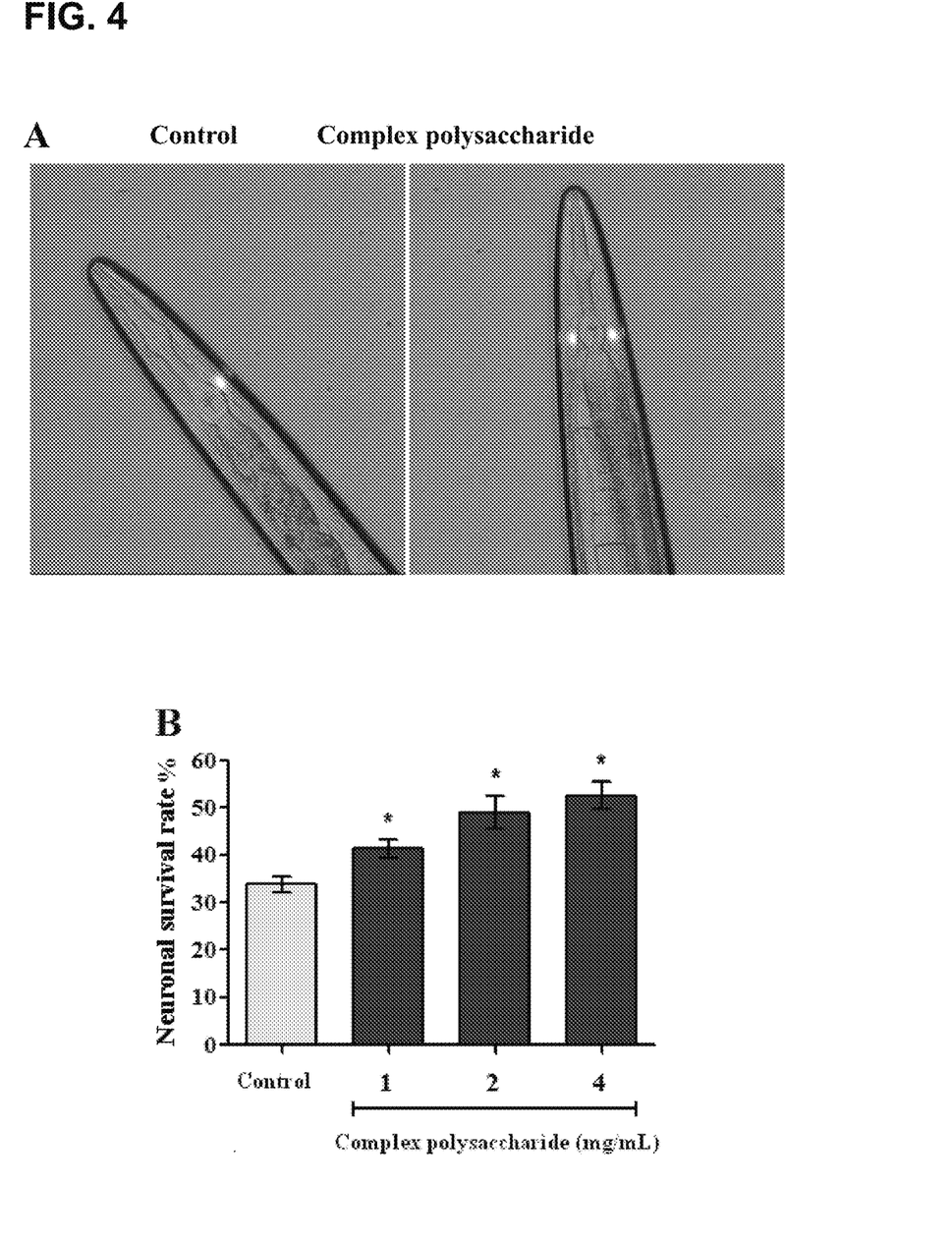
FIG. 4 is a characterization figure of the data of utilizing the ginseng and tuber fleeceflower root complex polysaccharide in Example 3 for inhibiting the toxicity of polyglutamine in C. elegans HA759 in vivo in Example 11, wherein FIG. 4A characterizes the representative figure of untreated and 2 mg/mL of complex polysaccharide-treated HA759 C. elegans ASH neurons, FIG. 4B characterizes 1 mg/mL, 2 mg/mL and 4 mg/mL of complex polysaccharide for inhibiting the polyglutamine aggregation toxicity in HA759 C. elegans in vivo, FIG. 4C characterizes 1 mg/mL, 2 mg/mL and 4 mg/mL of complex polysaccharide for alleviating the behavior defect caused by polyglutamine aggregation toxicity, wherein * represents $p<0.05$.

The results are as shown in FIG. 4A, the apoptosis of ASH neuron of polysaccharide untreated HA759 *C. elegans* takes place (fluorescent vanishes) because of polyQ aggregation, after complex polysaccharide is added, ASH neuron still survives (fluorescent exists). FIG. 4B show that, the survival rate of ASH neuron of untreated HA759 *C. elegans* after 3 d is 33.9%, while after the treatment with 1 mg/mL, 2 mg/mL and 4 mg/mL of complex polysaccharide, the survival rate of ASH neuron are improved to 41.3%, 49.1% and 52.7%, respectively. The results show that complex polysaccharide is able to inhibit the toxicity stress response of aggregation-feasible protein polyQ, has an effect of alleviating aging-related disorders.

Since ASH neuron has the avoiding activity to hyperosmosis, therefore when induced and blocked by hyperosmotic solution, ASH neuron non-apoptic *C. elegans* can retain the behavior character of avoiding hyperosmotic solution, while the *C. elegans* with ASH neuron dead will lose avoiding activity to hyperosmostic solution. Thus, by utilizing HA759 *C. elegans* model, it is possible to detect the alleviation effect of complex polysaccharide on the behavior defect induced by toxic protein. The complex polysaccharide prepared by Example 3, is added in a concentration of 1 mg/mL, 2 mg/mL and 4 mg/mL to L1 Phase HA759 larvae, respectively, an equal volume of S Medium is added to control group. After cultivated under 15° C. for 3 d, *C. elegans* is collected. With 8 M glycerol (hyperosmotic reagent), diacetylene (inducing reagent), sodium azide (anesthetic) are used to prepare chemotactic avoidance plate, the *C. elegans* after treatment are placed on the plate, after cultivated at 20° C. for 1.5 h, the distributed number of *C. elegans* are statistically counted. The formula of avoidance rate is calculated as follows: avoidance rate=(*C. elegans* numbe in avoidance region r/total number of *C. elegans*)×100%, avoidance rate is represented by mean±SD, one-way ANOVA analysis and Tukey post-hoc test are used to compare the difference between polysaccharide group and control group.

The results are as shown in FIG. 4C, there is 44.1% of C. elegans in control group demonstrates avoiding behavior around hyperosmotic glycerol solution, after the treatment with 1 mg/mL, 2 mg/mL and 4 mg/mL of complex polysaccharide, the avoidance rate of HA759 C. elegans is improved to 51.9%. 56.8% and 58.7%, respectively, which show that complex polysaccharide can alleviate the behavior defect induced by toxic protein polyQ, has the same result as in FIGS. 4A and 4B.

The aforesaid results show that, complex polysaccharide is able to inhibit Aβ and polyQ toxic protein stress injury on the level of neuron cell and Animal Behavior, which show that it has good effect for preventing aging-related disorders.

EXAMPLE 12

Heat Shock Proteins (HSPs) is a broad type of broadly existed and highly conserved molecule partner family, mainly play important role in the folding, assembly, transport, localization and degradation processes of proteins, in the mean time, involve in the regulation of several signaling pathway in the cell. Studies show that, in the aging individuals and many aging-related diseases, such as neurodegenerative diseases, the intracellular protein balance is out of balance, the activities of some heat block proteins are also reduced to some degree. Thus, by improving the expression or activity of heat block protein, it is possible to achieve the effects of delaying aging and disease progression. The complex polysaccharide prepared by Example 4, in an concentration of 2 mg/mL, after mixed homogenously with OP50, is spread on NGM culture dish, then L1 Phase CL2070 C. elegans (in vivo expresses hsp-16.2::GFP fusion protein) is added. After cultivated under 20° C. till L4 Phase, C. elegans is collected and paralyzed with sodium azide, then fixed, and placed on 2% agarose pad. Photo of C. elegans pharynx is taken by fluorescent microscope, Image J software is used to statistically count fluorescent density in pharynx. About 10 C. elegans are statistically counted in each treatment group, data is represented by mean±SD, T test is used to compare the difference between polysaccharide group and control group.

Figure 5:
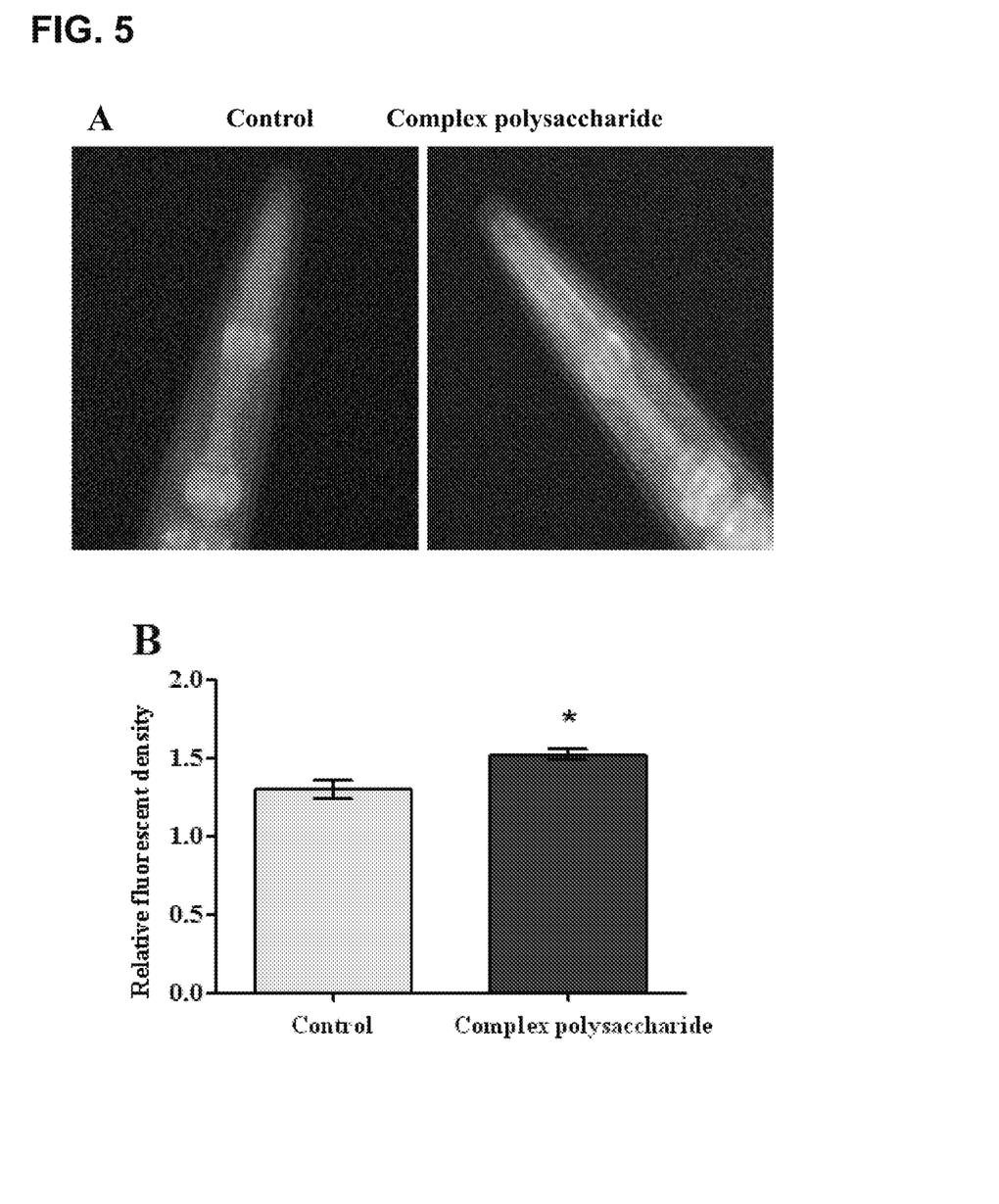
FIG. 5 is a characterization figure of the data of regulation effect of utilizing the ginseng and tuber fleeceflower root complex polysaccharide in Example 4 on the heat block protein in *C. elegans* in vivo in Example 12, wherein FIG. 5A characterizes the representative figure of the effect of 2 mg/mL of complex polysaccharide on the expression of HSP16.2 in *C. elegans* CL2070 in vivo, FIG. 5B characterizes 2 mg/mL of complex polysaccharide for promoting the expression of HSP16.2 in *C. elegans* CL2070 in vivo, wherein * represents p<0.05.

The results are as shown in FIG. 5A, in comparison with control group, after the treatment with complex polysaccharide, CL2070 C. elegans pharynx fluorescent level is improved obviously. The statistical result of FIG. 5B show that, after the treatment with 2 mg/mL of complex polysaccharide, the fluorescent density is improved from 1.31 to 1.52. The results show that, complex polysaccharide has an effect of promoting the expression of HSP16.2, the important member heat block protein family.

EXAMPLE 13

When biologically active polysaccharide acts on the cell, the cell will sense and process this active signal through a series of signaling cascade, thus the research to this signaling effect is essential to exploring the function of polysaccharide and modifying saccharides products. Recent researches show that, insulin signalling pathway besides regulating organism growth by controlling metabolic degree and biological synthesis process, but also regulates the core mechanism of organism life span directly, is highly conservative in evolution. Thus, selecting the representative crucial node daf-2, age-1 and daf-16 in the insulin signalling pathway, the corresponding C. elegans mutant strain is CB1370, TJ1052 and DR26, respectively, by studying the prolongation effect of complex polysaccharide on the life span of these three mutant strains, it is possible to explore its relationship with insulin signalling pathway. The complex polysaccharide prepared by Example 5, in a concentration of 2 mg/mL, is added to 5-FUDR treated L4 Phase CB1370, TJ1052 and DR26 larvae, respectively. An equal volume of S Medium is used to substitute polysaccharide solution in control group. The available 96-well plate is cultivated under 20° C., the start-up day of administration is regarded as Day 0, the survival status of C. elegans in each well is statistically counted every 2-4 d, until all of them die. The determination of the death status and the statistical method of the survival rate of C. elegans are as in Example 7.

Figure 6:
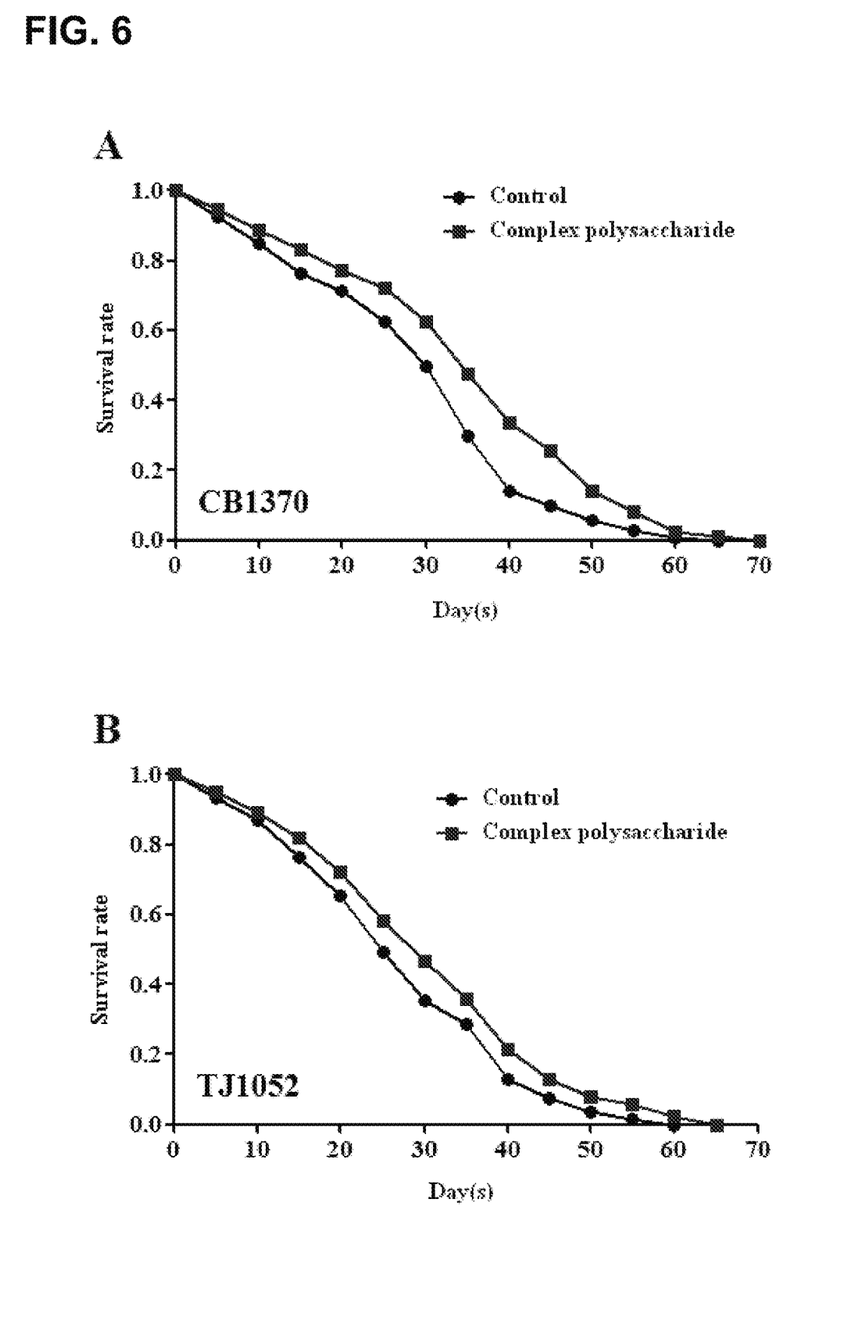
FIG. 6 is a characterization figure of the data of regulation effect of utilizing the ginseng and tuber fleeceflower root complex polysaccharide in Example 5 on the insulin signalling pathway in *C. elegans* in vivo in Example 13, wherein FIG. 6A characterizes the prolongation effect of 2 mg/mL of complex polysaccharide on the life span of *C. elegans* CB1370, FIG. 6B characterizes the prolongation effect of 2 mg/mL of complex polysaccharide on the life span of *C. elegans* TJ1052, FIG. 6C characterizes the effect of 2 mg/mL of complex polysaccharide on the life span of *C. elegans* DR26, FIG. 6D characterize 2 mg/mL of complex polysaccharide for promoting the entry of DAF-16 into the nucleus of *C. elegans* TJ356 in vivo.

The results are as shown in FIGS. 6A, 6B and 6C, complex polysaccharide in a concentration of 2 mg/mL not only can prolong the average life span of CB1370 C. elegans from 30.2 d to 34.8 d, but also prolong the average life span of TJ1052 C. elegans from 26.5 d to 29.2 d, but it is impossible to prolong the average life span of DR26 C. elegans. The results show that the prolongation effect of complex polysaccharide on the life span is related to DAF-16, but not related to DAF-2 and AGE-1.

Being a FOXO family transcription factor, DAF-16 is the pivot of many signaling pathways, which locates in the cytoplasm under normal condition, when activated, it enters into nucleus to perform the function of transcription factor, thus initiates serial down-stream gene expression, improves the stress ability of C. elegans, prolongs the life span of C. elegans under stress condition. TJ356 transgenic mutant strain broadly expresses DAF-16::GFP in the C. elegans tissue cells, when insulin signalling pathway is not activated, C. elegans demonstrates evenly diffusing green fluorescent, when insulin signalling pathway is activated, the nuclear localization of DAF-16 makes evenly diffusing fluorescent transformed into aggregation-like fluorescent points. Thus, this model is used to further confirm the regulation effect of complex polysaccharide on DAF-16. TJ356 C. elegans is synchronized to L1 Phase, the C. elegans density is adjusted with S Medium to about 20/10 μL, OP50 is added to make OD570≈0.4. The complex polysaccharide prepared in Example 5 is added into C. elegans, the final concentration of polysaccharide is 2 mg/mL, equal volume of S Medium is added into the control group. After cultivated under 20° C. for 48 h, C. elegans are collected and fixed on the agar pad, the GFP expression condition of each C. elegans is observed under a fluorescent microscope, each treatment group statistically analyzes about 20 C. elegans randomly.

The results are as shown in FIG. 6D, untreated TJ356 C. elegans demonstrate evenly diffusing green fluorescent all around, upon treatment with 2 mg/mL of complex polysaccharide, scattered fluorescent aggregation points are occurred around C. elegans, demonstrates that complex polysaccharide promotes the entry of DAF-16 into nucleus, further proves that complex polysaccharide is able to regulate the crucial node DAF-16 in the insulin signalling pathway.

As proved by the result of aforesaid C. elegans model test, the prepared complex polysaccharide is able to prolong the life span of C. elegans under normal, oxidation stress and toxic aggregation protein stress conditions effectively (Example 7), its effecting manner relates to reducing intracellular ROS level (Example 8), improving antioxidant enzyme activity (Example 9), reducing peroxide MDA content (Example 9), inhibiting the neurotoxicity and behavior defect induced by toxic protein (Examples 10 and 11), enhancing the activity of heat block protein (Example 12) and regulating the crucial node of insulin signalling pathway (Example 13). The results sufficiently show that the complex polysaccharide prepared by ginseng and tuber fleeceflower root has good effect for delaying aging and preventing relative disorders.

EXAMPLE 14

To the complex polysaccharide prepared by Example 1, appropriate amounts of lactalbumin, maltodextrin are added as required to prepare the health food or health-care food in powder form having a neuroprotecting efficacy, other conventional supplements can also be added to formulate into conventional dosage form.

The aforesaid examples are preferable embodiments of the present invention, but the embodiments of the present invention are not limited by the aforesaid examples, any other change, modification, substitution, combination, abbreviation made not departing from the spirit essence and principle of the present invention, is regarded as equivalent substitution manner, and are enclosed within the protection scope of the present invention.

What is claimed is:
1. A process for producing a ginseng and tuber fleeceflower root complex polysaccharide in the preparation of health-care food having aging reduction efficacies, consisting essentially of:
 a) providing ginseng root and tuber fleeceflower root at a ratio of 2:3-2:1, respectively,
 b) performing a water extraction of the ginseng root and tuber fleeceflower root at a ratio of 1:10, ginseng root and tuber fleeceflower root complex polysaccharide to water, respectively, at an extraction temperature of 90° C. for 4 hours to form an aqueous ginseng root and tuber fleeceflower root;
 c) concentrating the aqueous ginseng root and tuber fleeceflower root to form a concentrated liquid;
 d) using ethanol to perform an alcohol precipitation of the concentrated liquid, wherein the volume ratio of ethanol to concentrated liquid is 2:1-9:1, respectively to form an ethanol precipitation of the concentrated liquid; and
 e) allowing the ethanol precipitation of the concentrated liquid to stand overnight at 4° C. to precipitate and yield said ginseng and tuber fleeceflower root complex polysaccharide.

* * * * *